United States Patent [19]

Kuhstoss et al.

[11] Patent Number: 5,093,252

[45] Date of Patent: Mar. 3, 1992

[54] TRANSCRIPTION TERMINATOR AND RELATED RECOMBINANT DNA VECTORS AND TRANSFORMANTS

[75] Inventors: Stuart A. Kuhstoss; R. Nagaraja Rao, both of Indianapolis, Ind.

[73] Assignee: Eli Lilly and Company, Indianapolis, Ind.

[21] Appl. No.: 515,538

[22] Filed: Apr. 30, 1990

Related U.S. Application Data

[63] Continuation of Ser. No. 188,087, Apr. 27, 1988, abandoned, which is a continuation of Ser. No. 654,918, Sep. 27, 1984, abandoned.

[51] Int. Cl.$^5$ .................. C12N 15/00; C12N 15/11; C12N 15/70; C12N 15/76
[52] U.S. Cl. .................. 435/172.3; 435/91; 435/252.3; 435/252.33; 435/252.35; 435/320.1; 536/27; 935/39
[58] Field of Search .................. 435/91, 172.1, 172.3, 435/320.1, 252.3, 252.31, 252.35, 69.1, 71.2; 536/27; 935/6, 29, 31, 39, 75

[56] References Cited

U.S. PATENT DOCUMENTS

| | | | |
|---|---|---|---|
| 4,495,280 | 1/1985 | Bujard et al. | 435/6 |
| 4,680,265 | 7/1987 | Birmingham et al. | 435/172.3 |
| 4,710,464 | 12/1987 | Belagaje et al. | 435/91 |

OTHER PUBLICATIONS

McKenney et al, "A System to Study Promoter and Terminator Signals Recognized by Escherichia coli RNA Polymerase", in *Gene Amplification and Analysis*, vol. 2, Chirikjian et al (ed.), Elsevier/North-Holland, Amsterdam (1981), pp. 383–415.
Holmes, W. M. et al., 1983, *Cell* 32: 1029–1032.
Chater, K. et al., 1982, *Gene* 19: 21–32.
Chater, K. et al., 1981, *Gene* 14: 183–194.
Russell and Bennett, 1982, *Gene* 20: 231–243.
Rosenberg, M. et al., 1983, *Science* 222: 734–739.
Das, A. et al., 1976, *Proc. Natl. Acad. Sci.* 78: 1959–1963.
Stueber and Bujard, 1982, *EMBO Journal* 1: 1399–1404.
Gentz, R. et al., 1981, *Proc. Nat. Acad. Sci.* 78: 4936–4940.
Beck, E. et al., 1981, *Gene* 19: 327–336.
Kuhstoss and Rao, 1983, *Gene* 26: 295–299.
Richardson, M. et al., 1982, *Gene* 20: 451–457.

*Primary Examiner*—James Martinell
*Attorney, Agent, or Firm*—Joseph A. Jones; Leroy Whitaker

[57] ABSTRACT

A transcription terminator is disclosed comprising a DNA sequence capable of functioning as a transcription terminator in a microorganism of the order Actinomycetales. These transcription terminators are functional in both gram-positive and gram-negative microorganisms, especially *Streptomyces ambofaciens*. Additionally, a series of recombinant DNA cloning vectors suitable for isolating the disclosed transcription terminators are set forth.

40 Claims, 8 Drawing Sheets

Restriction Site Map of
Plasmid pKC331
(47.2kb)

Restriction Site Map of
Plasmid pKC377
(5.0kb)

Restriction Site Map of
Plasmid pKC424
(11.7kb)

Restriction Site Map of
Plasmid pKC326
(9.7kb)

Restriction Site Map of
Plasmid pKC345
(10.8kb)

Restriction Site Map of
Plasmid pKC354
(12.5kb)

Restriction Site Map of
Plasmid pKC356
(11kb)

Restriction Site Map of
Plasmid pKC425
(11.7kb)

TRANSCRIPTION TERMINATOR AND RELATED RECOMBINANT DNA VECTORS AND TRANSFORMANTS

BACKGROUND OF THE INVENTION

This application is a continuation of application Ser. No. 07/188,087, filed on Apr. 27, 1988, now abandoned which is a continuation of application Ser. No. 06/654,918, filed on Sept. 27, 1984, now abandoned.

This invention relates to a DNA sequence capable of terminating transcription in a variety of microorganisms, including gram-positive microorganisms. This invention also relates to recombinant DNA cloning vector systems for isolating a DNA sequence capable of functioning as a transcription terminator and such microorganisms and recombinant vectors in which the sequence can be used.

In the creation of recombinant expression vector systems, it has been found to be desirable to have additional products and methods with which to control the transcription and translation of genetic material in microorganisms, particularly in gram-positive microorganisms. For example, it would be desirable to be able to control selectively the transcription of various portions of a recombinant DNA cloning vector. As reported in the literature, the identification and isolation of transcription terminators operable in gram-negative microorganisms, particularly *Escherichia coli*, have allowed researchers to conduct experiments designed to identify and test the signal strength of various promoters. See, e.g., Gentry et al., Proc. Nat'l. Acad. Sci. U.S.A., Vol. 78:4936 (1981). Identification of a transcription terminator capable of functioning in Gram-positive microorganisms would allow similar operations to be conducted in such microorganisms.

The transcription terminator would provide advantages if it were bi-directional, i.e., capable of functioning in either orientation. This would increase the probability that the terminator, upon ligation into a vector, would function and allow regulation of the expression of genes in the vector. Use of a transcription terminator in this manner allows for selective expression of various genes located in a recombinant vector system and allows for the functional control of various portions of the recombinant vector system. The ability to control selectively the expression of portions of a plasmid in gram-positive microorganisms would increase the value and flexibility of such organisms as hosts for the biological manufacture of gene products.

In particular, it has been found that a transcription terminator capable of controlling transcription in gram-positive microorganisms would be useful in either reducing or eliminating transcription read-through downstream of a gene of interest or in reducing or eliminating, in a reversible manner, expression of a downstream gene by placement of the terminator upstream from the gene and its promoter. It has also been noted that a terminator which is bi-directional, i.e., capable of operating in either orientation, would, if placed downstream of a gene of interest, prevent transcriptional read-through in the opposite direction, i.e., prevent transcription initiated by a downstream promoter in the opposite direction upstream through the gene.

Products and methods that encourage maximization of the copy number of a recombinant vector are also desirable. It has been noted that under certain conditions, recombinant vectors do not replicate with any predictable frequency despite the presence of an origin of replication appropriate for the host microorganism. It is believed that such vectors do not replicate properly because of the presence of a strong promoter that causes the transcription of large portions of the vector. The presence of a strong, active promoter can interfere with the normal functioning of the origin of replication. In these situations, the rapid division rate of the host microorganisms quickly dilutes the number of vectors contained in the microorganisms. This prevents the recombinant vector from being present in commercially feasible quantities and could ultimately result in loss of the vector.

The present invention overcomes these problems by providing a DNA sequence which is capable of functioning as a transcription terminator in a variety of microorganisms, including gram-positive microorganisms. This transcription terminator affords selective control over portions of recombinant DNA cloning vectors and is capable of preserving the operation of an origin of replication in a recombinant DNA cloning vector containing a strong promoter. Additionally, the transcription terminator of the present invention is capable of functioning in both gram-positive and gram-negative microorganisms. This ability further enhances the usefulness of the transcription terminator since certain desirable manipulations of recombinant vectors can be conducted in well studied gram-negative microorganisms such as *E. coli*.

The transcription terminator of the present invention is particularly useful in recombinant vector systems designed for microorganisms of the genus Streptomyces. Such microorganisms are of great importance as research and commercial host organisms. Streptomyces microorganisms are characterized, inter alia, by a mycelial form of growth that normally culminates in sporulation. Microorganisms of the genus Streptomyces produce a wider range of antibiotics than microorganisms of any other genus. Additionally, some members of the genus Streptomyces also produce exoenzymes. Therefore, mechanisms which afford increased ability to control and propagate recombinant vector systems in Streptomyces have long been sought.

SUMMARY OF THE INVENTION

An object of the present invention is to provide a portable DNA sequence capable of functioning as a transcription terminator in microorganisms of the genus Streptomyces when inserted into a recombinant DNA cloning vector for such organisms. In a preferred embodiment, the transcription terminator is bi-directional, i.e., has the ability to terminate transcription initiated in either direction. An additional object of the invention is to provide a recombinant vector system in which a transcription terminator is present to afford selective control over the expression of various genes present in the system. Accordingly, transcription terminators of the present invention may be positioned in the recombinant DNA cloning vectors to reduce or eliminate transcriptional read-through into a DNA sequence downstream of the gene of interest and/or may be positioned upstream from the gene of interest to similarly prevent read-through transcription. The bi-directional nature of the terminator also allows it to prevent transcriptional read-through from a second promoter which is located downstream but which initiates transcription in the opposite direction through the gene of interest.

A further object of the present invention is to provide a transcription terminator which reduces the interference sometimes imposed by a strong promoter on the functioning of an origin of replication and the ability of the vector to replicate. The recombinant DNA cloning vectors suitable for use in the isolation of a portable DNA sequence capable of functioning as a transcription terminator in microorganisms of the genus Streptomyces as well as the assorted vectors and transformants containing the portable terminators also comprise the present invention.

Additional objects and advantages of the invention will be set forth in part in the description which follows and will be apparent to those skilled in the art. The objects and advantages may also be realized and attained by means of the instrumentalities and combinations particularly pointed out in the appended claims.

To achieve the objects in accordance with the purposes of the invention, a transcription terminator is provided comprising a portable DNA sequence capable of functioning as a transcription terminator in a microorganism of the genus Streptomyces. Preferably, the transcription terminator is capable of reducing or eliminating transcription in microorganisms of the order Actinomycetales and, in increasing order of preference, those of the family Streptomycetaceae, the genus Streptomyces and the species *Streptomyces ambofaciens*. Additionally, terminators are capable of reducing or eliminating transcription in microorganisms selected from the group consisting of Streptomyces, Norcardia and Cephalosporium. Preferred transcription terminators are also capable of reducing or eliminating transcription in gram negative microorganisms and are particularly useful for reducing or eliminating transcription in microorganisms of the genus Escherichia.

In a preferred embodiment of the present invention, the transcription terminator is a portable ~700 base pair (bp) DNA sequence isolated from a bacteriophage, preferably from the Streptomyces bacteriophage φC31. Transcription terminators of the present invention find particular application in recombinant DNA cloning vectors in which they serve to reduce or eliminate superfluous transcription and subsequent expression of large portions of vector DNA. The instant transcription terminators are also suitable for use in recombinant DNA cloning vectors to correct problems with copy number caused by read-through transcription.

Therefore, a novel recombinant DNA cloning vector is disclosed comprising an origin of replication for a microorganism, a promoter, at least one gene associated with and capable of being transcribed by the promoter, and a sequence of portable DNA capable of functioning as a transcription terminator in a microorganism of the genus Streptomyces. The portable DNA is located in the cloning vector in a position such that it is capable of reducing or eliminating read-through transcription of all or part of a gene when the cloning vector is transformed into a microorganism. Recombinant DNA cloning vectors useful in processes for identifying transcription terminators operable in microorganisms in the genus Streptomyces are also disclosed.

It is understood that both the foregoing general description and the following detailed description are exemplary and explanatory only and are not restrictive of the invention, as claimed. The accompanying drawings, which are incorporated in and constitute a part of this specification, illustrate various embodiments of the invention and, together with the description, serve to explain the principles of the invention.

DETAILED DESCRIPTION OF THE PREFERRED EMBODIMENTS

Figure 1:
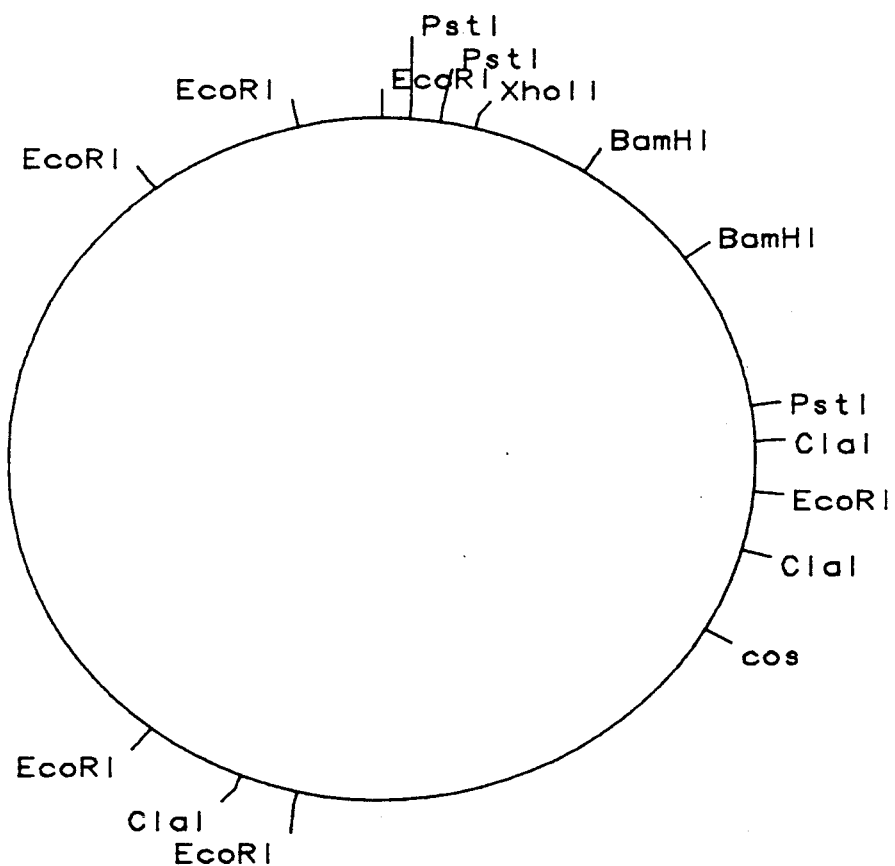
FIG. 1 is a restriction map of plasmid pKC331.

Reference will now be made in detail to the presently preferred embodiments of the invention, which together with the following examples, serve to explain the principles of the invention.

For purposes of the present invention, as disclosed and claimed herein, the following terms are as defined as follows:

Recombinant DNA Expression Vector—any autonomously replicating agent, including but not limited to plasmids, comprising a DNA molecule to which one or more additional DNA segments can be or have been added.

Transformation—the introduction of DNA into a recipient host cell.

Transformant—a recipient host cell that has undergone transformation.

Restriction Fragment—any linear DNA generated by the action of one or more restriction enzymes.

Transriptional and Translational Activating Sequence—a DNA sequence that directs the transcription of DNA into messenger RNA (m-RNA) and the subsequent translation of the m-RNA into a polypeptide.

Functional Polypeptide—a recoverable bioactive entirely heterologous or homologous polypeptide or precursor, a recoverable bioactive polypeptide comprising a heterologous polypeptide and a portion or whole of a homologous polypeptide, or a recoverable bioinactive fusion polypeptide comprising a heterologous polypeptide and a bioinactivating homologous polypeptide which can be specifically cleaved.

Fused Gene Product—a recoverable heterologous polypeptide which is fused with a portion or whole of a homologous polypeptide.

As noted above, the present invention relates to a portable DNA sequence capable of functioning as a transcription terminator in a variety of host microorganisms. "Portable DNA sequence" in this context is intended to refer either to a synthetically produced nucleotide sequence or to a restriction fragment. In particular, the present invention relates to a transcription terminator comprising a portable DNA sequence capable of functioning as a transcription terminator in a microorganism of the genus Streptomyces when inserted into a recombinant vector system.

The methods and the transcription terminators of the present invention are useful for enhancing the production of almost any functional polypeptide such as, for example, human proinsulin, human insulin A-chain, human insulin B-chain, human growth hormone, bovine growth hormone, porcine growth hormone, growth hormone releasing factor, human interferon, Interleukin I, Interleukin II, IGF I, IGF II, urokinase, tissue plasminogen activator, viral antigen, polypeptide enzyme, polypeptide antibody, polypeptide hormone and an enzyme in a metabolic pathway, by means of recombinant DNA technology. Additionally, the methods and transcription terminators of the present invention are useful for correcting copy number problems associated with read-through transcription.

Preferably, the transcription terminator is capable of reducing or eliminating superfluous transcription in host microorganisms of the genus Streptomyces. However, the transcription terminators and recombinant DNA cloning vectors of the present invention are not limited for use in a single species or strain of Streptomyces. To the contrary, the transcription terminators and the vectors are broadly applicable and can be used with host cells of many *Streptomyces taxa*, particularly restrictionless strains of economically important taxa that produce antibiotics such as aminoglycoside, macrolide, β-lactam, polyether and glycopeptide antibiotics. Host cells of restrictionless strains lack restriction enzymes and, therefore, do not cut or degrade plasmid DNA upon transformation. For purposes of the present application, host cells containing restriction enzymes that do not cut any of the restriction sites of the present vectors are also considered restrictionless. Such restrictionless strains are readily selected and isolated from *Streptomyces taxa* by conventional procedures well-known in the art, for example those set forth in Lomovskaya et al., Microbiological Reviews 44:206 (1980), specifically incorporated herein by reference.

Preferred host cells of restrictionless strains of *Streptomyces taxa* that produce aminoglycoside antibiotics, in which the present transcription terminators and vectors are especially useful and can be transformed, include restrictionless cells of, for example: *S. chrestomyceticus* (aminosidine), *S. griseoflavus* (antibiotic MA 1267), *S. microsporeus* (antibiotic SF-767), *S. ribosidificus* (antibiotic SF733) *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. albogriseolus* (neomycins), *S. tenebrarius* (tobramycin, apramycin), *S. albus* var. *metamycius* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. fradiae* (hybrimycins, neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex) and *S. canus* (ribosyl paromamine).

Preferred host cells of restrictionless strains of *Streptomyces taxa* that produce macrolide antibiotics, in which the present transcription terminators and vectors are especially useful and can be transformed, include restrictionless cells of, for example: *S. caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetylleukomycin, espinomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (spiramycin, foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), *S. albireticuli* (carbomycin).

Preferred host cells of restrictionless strains of *Streptomyces taxa* that produce β-lactam antibiotics, in which the present transcription terminators and vectors are especially useful and can be transformed, include restrictionless cells of, for example: *S. lipmanii* (A16884, MM4550, MM13902), *S. clavuligerus* (A16886B, calvulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromyorphus* and *S. panayensis* (C2081X); *S. cinnamonensis, S. fimbriatus, S. halstedii, S. rochei* and *S. viridochromogenes* (cephamycins A, B), *S. cattleya* (thienamycin), and *S. olivaceus, S. flavovirens, S. flavus, S. fulvoviridis, S. argenteolus* and *S. sioyaensis* (MM 4550 and MM 13902).

Preferred host cells of restrictionless strains of *Streptomyces taxa* that produce polyether antibiotics, in which the present transcription terminators and vectors are especially useful and can be transformed, include restrictionless cells of, for example: *S. albus* (A204, A28695A and B, salinomycin), *S. hygroscopicus* (A218, emericid, DE3936), A120A, A28695A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (hysocellin), *S. flaveolus* (CP38936), *S. mutabilis* (S-11743a) and *S. violaceoniger* (nigericin).

Preferred host cells of restrictionless strains of Streptomyces (or related genera such as, for example, Nocardia) that produce glycopeptide antibiotics, in which the present transcription terminators and vectors are especially useful and can be transformed, include restrictionless cells of, for example: *Nocardia orientalis* and *S. haranomachiensis* (vancomycin); *Nocardia candidus* (A-35512, avoparcin), *S. eburosporeus* (LL-AM 374), *S. virginiae* (A41030) and *S. toyocaensis* (A47934).

Preferred host cells of other restrictionless strains of *Streptomyces taxa*, in which the present transcription terminators and vectors are especially useful and can be transformed, include restrictionless cells of, for example: *S. coelicolor, S. granuloruber, S. roseosporus, S. lividans, S. tenebrarius, S. acrimycins, S. glaucescens, S. parvilin, S. pristinaespiralis, S. violaceoruber, S. vinacous, S. espinosus, S. azureus, S. griseofuscus, S. fradiae* and *S. ambofaciens.*

Additionally, preferred transcription terminators are capable of reducing or eliminating transcription in host microorganisms of different genera, orders and families. For example, transcription terminators capable of reducing or eliminating transcription in both gram-positive and gram-negative host microorganisms are preferred for use in the present invention. Those transcription terminators which are particularly preferred are capable of reducing or eliminating transcription both in host microorganisms of the genus Streptomyces and in microorganisms of the genus Escherichia. In particular, *E. coli* strains *E. coli* K12, *E. coli* K12 HB101, *E. coli* K12 RR1, *E. coli* K12 RV308, *E. coli* K12 C600, *E. coli* K12 C600 $R_k$-$M_k$-, *E. coli* K12 MM294, and *E. coli* K12 JA221 may serve as host microorganisms, as well as any other *E. coli* strains mentioned in the Examples set forth below.

In the present invention, a transcription terminator is an identifiable, portable DNA sequence that includes a nucleotide base pair sequence necessary for reducing or eliminating transcription. It is preferred that the transcription terminator not have an excessive number of extraneous base pairs either preceding or subsequent to the operative sequence. However, if the nucleotide sequence forming the transcription terminator is composed of a small number of base pairs, extraneous base pairs may precede and/or succeed the operative sequence provided these extraneous base pairs do not affect the ability of the operative sequence to function as a transcription terminator.

In a preferred embodiment of the present invention, the transcription terminator is bi-directional, i.e., capable of eliminating transcription in either orientation. This characteristic offers several advantages. In part, it increases the practical efficiency of the terminator because all terminators inserted into the vector are functional as opposed to only half if a uni-directional terminator were used. Additionally, a bi-directional terminator is capable of reducing or eliminating transcription that is occurring in a clockwise direction while at the same time reducing or eliminating transcription which is occurring in a counterclockwise direction. Therefore, if a vector has multiple promoters, at least one of which initiates transcription in a clockwise direction and at least one of which initiates transcription in a counterclockwise direction, the preferred terminator can reduce or eliminate transcription initiated by either and/or both promoters simultaneously.

A preferred transcription terminator of the present invention is a portable DNA sequence of approximately 700 bp. This nucleotide sequence may be isolated from plasmid pKC331 or pKC377, contained in microorganisms on deposit at the Agricultural Research Culture Collection, Peoria, Ill., under NRRL Accession Nos. B-15828 and B-15885, respectively, using methods known to those of ordinary skill in the art. Additionally, other terminators within the present scope can also be obtained by following methods for identification of a DNA sequence capable of functioning as a transcription terminator as set forth below. A restriction site map of each of plasmids pKC331 and pKC377 is presented respectively in FIGS. 1 and 2 of the accompanying drawings.

Terminator sequences of the present invention can be obtained from viral, eukaryotic or prokaryotic sources or may be synthetically constructed by conventional chemical methods. In one embodiment, the terminator is preferably obtained from a prokaryotic organism, more preferably from a gram-positive microorganism. In another preferred embodiment of the present invention, the transcription terminator is obtained from a bacteriophage, more preferably from a Streptomyces bacteriophage and, in a particularly preferred embodiment, from bacteriophage φC31. The entire genome of φC31 has been incorporated into plasmid pKC331. The plasmid thus serves as a preferred source of φC31 DNA and can be obtained from NRRL as described above.

In one embodiment of the present invention, the transcription terminator has a series of base pairs, both preceding and following the nucleotide sequence which is capable of reducing or eliminating transcription, that are recognized by a restriction endonuclease unique to the recombinant vector into which the terminator is inserted. This allows for the easy excision of the terminator from the vector. In an alternative embodiment, the nucleotide base pair sequences bracketing the operative portion of the terminator sequence are selected such that the base pair sequence which precedes the terminator sequence is recognized by one restriction endonuclease and the base pair sequence which follows the terminator sequence is recognized by a second restriction endonuclease. Preferably, although not required, both restriction sites should be unique to the vector. In this embodiment, new genetic material can be inserted either immediately preceding or immediately following the operative sequence. The choice of appropriate base pair sequences to form the restriction sites is generally within the capabilities of one of ordinary skill in the art in view of published reports of the sequences recognized by particular restriction endonucleases.

The transcription terminator can be inserted downstream from a stop codon of a gene whose expression is to be enhanced. The terminator should be sufficiently distant so as not to interfere with transcription or translation of the gene yet close enough so as to prevent read-through transcription. A position 10–20 bp downstream from the stop codon is preferred. The transcription terminator can also be inserted upstream from the transcriptional and translational activating sequence of the gene. The terminator should be sufficiently upstream so as to stop other promoters from reading through and interfering with the expression of the gene of interest. A position 10–20 bp upstream from the expression control region is preferred.

The terminator may also be positioned between a promoter and its associated gene to eliminate or reduce transcription. In this embodiment, the expression of a gene can be selectively controlled by the presence or absence of the terminator. In a vector that contains at least two genes, the terminator may be positioned so that the transcription of at least one gene is reduced or eliminated while, at the same time, the transcription of at least one other gene is unaffected. This position eliminates downstream transcriptional read-through and also prevents transcriptional read-through of the gene of interest in the opposite direction caused by a downstream promoter. The transcription terminators may also be positioned in a vector both upstream and downstream of the gene or genes of interest. In this embodiment, expression of the bracketed gene or genes of interest is enhanced.

To insert the transcription terminators of the present invention into a recombinant cloning vector, it is preferred that an unique endonuclease restriction site be created in a recombinant vector system into which the terminator is to be inserted. The creation of a unique restriction site in the vector may be accomplished by techniques generally employed by those skilled in the art. Selection of the particular technique for creation of the unique restriction site, and the actual nucleotide base pair sequence to be inserted to create a unique restriction site in the recombinant vector, will generally be within the capabilities of one of ordinary skill in the art based upon the insights gained through study of the examples hereinafter set forth and the characteristics of the recombinant vector system that is being employed.

Particular Streptomyces recombinant DNA cloning vectors in which the present terminators can be cloned and used are set forth in Table 1. The list is intended to exemplify various vectors and does not limit the present invention in any way. Various *E. coli* vectors can also be used in accordance with the present disclosure. Such vectors include, but are not limited to, plasmids pBR322, pBR324, pBR325, pBR328, pUC8 and pDR720.

TABLE 1

| Streptomyces Vectors | | |
|---|---|---|
| Vector | Source | Accession Number |
| SCP2 | *Streptomyces coelicolor* A3(2) | NRRL* 15042 |
| SCP2* | *Streptomyces coelicolor* M110 | NRRL 15041 |
| pEL7 | *Streptomyces ambofaciens*/pEL7 | NRRL 12523 |
| pUC6 | *Streptomyces espinosus* | NRRL 11439 |
| pUC3 | Streptomyces 3022A | NRRL 11441 |
| SLP1 | *Streptomyces lividans* | NCIB** 11417 |
| pNM100 | *Streptomyces virginiae* | NRRL 15156 |
| pEL103 | *Streptomyces granuloruber* A39912.13/pEL103 | NRRL 12549 |

*Agricultural Research Culture Collection (NRRL), 1815 North University Street, Peoria, Illinois 61604, United States of America
**National Collection of Industrial Bacteria (NCIB), Torry Research Station, Post Office Box 31, 135 Abbey Road, Aberdeen AB98DG, Scotland, United Kingdom The transcription terminators of the present invention are not limited to reducing or eliminating transcription initiated by a particular promoter. In fact, transcription from almost any promoter, such as, for example, the trp, lac, lpp, phage (such as pL and pR), TAC, β-lactamase, *Bacillis veg*, Staphylococcus nuclease or prokaryotic, eukaryotic and viral promoters can be terminated by use of the present invention. The aforementioned promoters in no way limit the present invention since other promoters can be isolated from naturally-occurring plasmids or can be created by recombinant techniques such as gene fusion as set forth in Rosenberg et al., (1983), Science, 222:734.

The preferred transcription terminators of the present invention, such as those derived from bacteriophage DNA and those contained in plasmids pKC424 and pKC425, have the added advantage of operating as transcription terminators regardless of their orientation in a recombinant plasmid. Indeed, these transcription terminators are functional in either orientation in both gram-positive microorganisms, such as *Streptomyces ambofaciens* and gram-negative microorganisms, such as *E. coli*. This feature greatly simplifies construction of terminator-containing plasmids. A restriction site map of plasmid pKC424 is presented in FIG. 3 of the accompanying drawings.

Portable DNA sequences capable of functioning as transcription terminators in gram-positive microorganisms can be identified by the following method which comprises a) treating a recombinant cloning vector containing a first DNA sequence coding for the expression of an identifiable characteristic with a restriction endonuclease capable of cleaving the recombinant plasmid at a restriction site located downstream from the promoter responsible for initiating transcription of the first DNA sequence;

b) inserting into the recombinant vector cleavage site a second DNA sequence suspected of being capable of functioning as a transcription terminator;

c) transforming the recombinant vector containing the first and second DNA sequences into a gram-positive microorganism capable of expressing the first DNA sequence in the absence of the second DNA sequence and then providing the microorganism with the conditions appropriate for expression and growth; and d) identifying microorganisms possessing the recombinant vector containing the second DNA sequence which are incapable of expressing the first DNA sequence.

Recombinant DNA cloning vector pKC388 is particularly suitable for use in identifying transcription terminators. This is done by cloning fragments of φC31 or other suitable DNA into plasmid pKC388. The resultant plasmids are analogous to plasmids pKC424 and pKC425 and can be conventionally screened for terminator activity in accordance with the following Examples.

It is to be understood that application of the teachings of the present invention to a specific microorganism will be within the capabilities of one having ordinary skill in the art in light of the teachings contained herein. Detailed construction protocols and methods for constructing the present terminators, vectors and transformants appear in the following examples.

EXAMPLE 1

Starting Materials

Plates, Media, Reagents

TYAp100—TY plates or TY broth with ampicillin at a concentration of 100 mg/ml.

TYAp100Nm25—TYAp100 plus neomycin at a concentration of 25 mg/ml.

R2 Plates 10.3% Sucrose, 0.025% $K_2SO_4$, 1% Glucose, 0.2% L-asparagine, 0.01% casamino acids, 0.025M TES (pH 7.2), 0.02M $CaCl_2$, 0.005% $KH_2PO_4$, 50 mM $MgCl_2$, 2.2% agar, Trace elements (Per Liter: 40 mg $ZnCl_2$, 200 mg $FeCl_3.6H_2O$, 10 mg $CuCl_2.2H_2O$, 10 mg $MnCl_2.4H_2O$, 10 mg $Na_2B_4O_7.10H_2O$, 10 mg $(NH_4)MO_{24}.4H_2O$.

R2 Overlays 10.3% Sucrose 50 mM MgCl$_2$
20 mM CaCl$_2$
0.025M TES (pH 7.2)
0.41% agar P Medium 10.3% Sucrose, 0.025% K$_2$SO$_4$, 0.203% MgCl$_2$, 0.005% KH$_2$PO$_4$, 0.025M TES (pH 7.2), CaCl$_2$ (0.278%)

Restriction Enzyme Buffers

AvaI
60 mM NaCl, 10 mM Tris (pH 8.0), 10 mM DTT, 10 mM MgCl$_2$
BglII
60 mM NaCl, 10 mM Tris (pH 7.4), 10 mM MgCl$_2$, 10 mM DTT
EcoRI
100 mM Tris (pH 7.5), 50 mM NaCl, 10 mM MgCl$_2$
PvuII
60 mM NaCl, 10 mM Tris (pH 7.5), 10 mM MgCl$_2$, 10 mM DTT
SacI
10 mM MgCl$_2$, 10 mM Tris (pH 7.4), 10 mM DTT
SmaI
20 mM KCl, 10 mM Tris (pH 8.0), 10 mM MgCl$_2$, 10 mM DTT
XhoII
10 mM Tris (pH 7.5), 10 mM MgCl$_2$, 10 mM DTT, 0.01% Triton X-100
PstI
150 mM NaCl, 10 mM Tris (pH 7.9), 10 mM MgCl$_2$, 10 mM DTT
EcoRI
100 mM Tris (pH 7.5), 50 mM NaCl, 10 mM MgCl$_2$
HindIII
60 mM NaCl, 10 mM Tris (pH 7.5), 10 mM MgCl$_2$, 10 mM DTT
AhaIII
75 mM NaCl, 10 mM Tris (pH 8.0), 10 mM MgCl$_2$, 10 mM DTT
BamHI
150 mM NaCl, 10 mM Tris (pH 7.9), 10 mM MgCl$_2$
HaeIII
50 mM NaCl, 10 mM Tris (pH 7.4), 10 mM MgCl$_2$, 10 mM DTT
RsaI
50 mM NaCl, 10 mM Tris (pH 8.0), 10 mM MgCl$_2$, 10 mM DTT Other Buffers TE
10 mM Tris (pH 8.0), 1 mM EDTA
Ligation Buffer
50 mM Tris (pH 7.8), 10 mM MgCl$_2$, 20 mM DTT, 1 mM ATP T4 DNA Polymerase Buffer 67 mM Potassium acetate, 33 mM Tris-acetate (pH 7.8), 10 mM Magnesium acetate 10x IBI BAP buffer 0.5M Tris pH 8.0, 0.5M NaCl 10X Denharts 0.2% Ficoll (Mol. weight 400,000)
0.2% Polyvinylpyrrolidine
0.2% BSA

1X SSPE 0.18M NaCl
1 mM EDTA
10 mM Sodium Phosphate, pH 7.7

Pre-hybridization mix

5X SSPE
50% deionized formamide
5X Denharts
0.05% SDS
100 μg/ml boiled salmon sperm DNA Hybridization mix Prehybridization mix and probe Column Buffer 10 mM Tris, pH 8.0
1 mM EDTA
30 mM NaCl
0.2% SDS

MOPS 7

10 mM MOPS (morpholinopropane sulfonic acid), pH 7.0
10 mM RbCl$_2$

MOPS 6.5

0.1M MOPS, pH 6.5
50 mM CaCl$_2$
10 mM RbCl$_2$

EXAMPLE 2

Construction of pKC377

Plasmid pKC331 contains the entire bacteriophage φC31 genome and serves as a source of φC31 DNA for purposes of the present invention.

Figure 2:
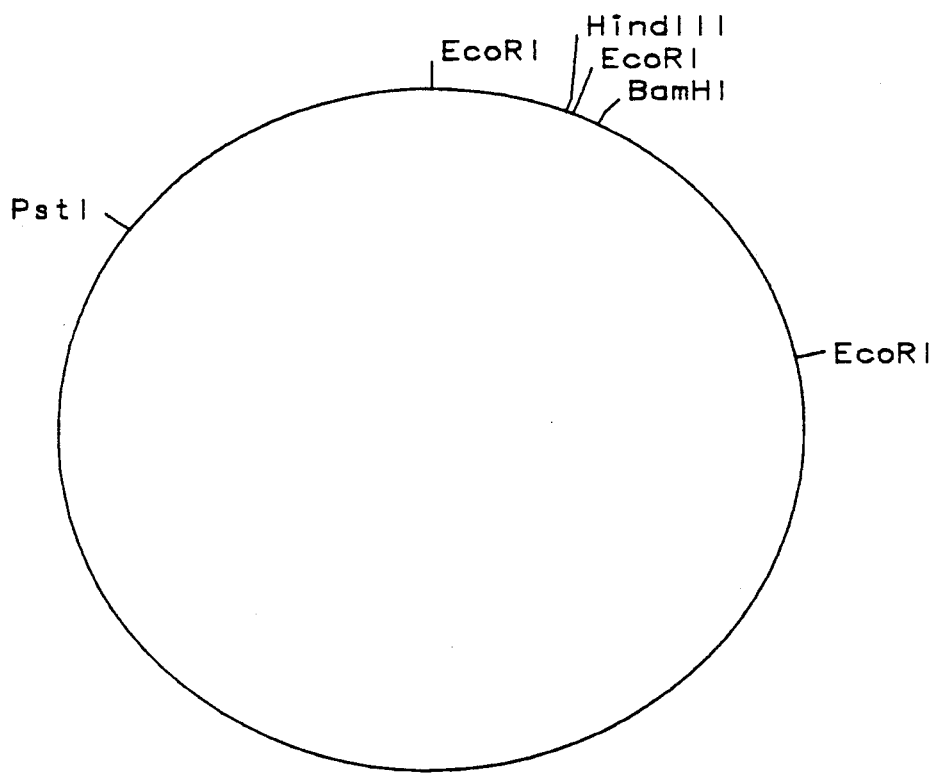
FIG. 2 is a restriction map of plasmid pKC377.

Cut 160 μg pKC331, set forth in FIG. 1 and available in *E. coli* K12 BE447/pKC331, on deposit at Agricultural Research Culture Collection (NRRL), Peoria, Ill., under Accession No. B-15828, with 80 U HaeIII in 800 μl at 37° C. Take one-third of total reaction mixture (267 μl) at 8, 10 and 12 minute intervals. Stop the reaction by adding the reaction mixture to 13.3 μl of 0.5M EDTA, resulting in a 25 mM final EDTA concentration, and heating at 70° C. for 10 minutes.

Cut 160 mg. pKC331 with 60 U RsaI in 800 μl at 37° C. Take one-third of the total reaction mixture at 3, 5 and 7 minute intervals. Stop the reaction by the addition of EDTA and heat as for the HaeIII digestion.

Ethanol precipitate the DNA by the addition of one-tenth volume of 3M sodium acetate (i.e. 5 μl NaOAc for 50 μl DNA solution). Add 3 volumes of ethanol (i.e., 150 μl for 50 μl DNA solution). Chill in dry ice-isopropanol bath. Centrifuge 5 minutes in an Eppendorf microfuge. Remove the supernatant and wash pellet with ethanol. After drying the pellet, dissolve the DNA obtained from each time point in 100 μl TE and pool all the HaeIII and RsaI-cut DNA.

Cut approximately 3.8 μg of pDR720, available from PL Biochemicals, 1037 W. McKinley Ave., Milwaukee, Wisc. 63205, with 10 U SmaI for one hour at 37° C. in a volume of 10 μl. Ethanol precipitate the DNA using the procedure set forth above. Add 10 μl of the pooled, partially-cut pKC331 DNA, and ligate overnight at 16° C. in 20 μl volume with 1200 U T4 DNA ligase.

Transform competent BE1368 cells (*E. coli* C600 galK; available from PL Biochemicals) with 10 μl of the ligated DNA. To form competent cells, grow the cells overnight at 30° C. with no shaking in TY media with 20 mM MgCl$_2$. Use this culture to inoculate a flask containing TY with 20 mM MgCl$_2$ (1% inoculum). Grow at 37° C. with shaking until absorbance at 550 nm is about 0.5. Centrifuge at 6000 rpm in a SS34 rotor for five minutes at 4° C. Decant the supernatant and resuspend the pellet in ½ volume of MOPS pH 7 that has been kept on ice. Centrifuge 6000 rpm for five minutes at 4° C. Decant the supernatant. Resuspend the pellet in ½ volume of cold MOPS pH 6.5. Hold the suspension for fifteen minutes on ice. Centrifuge at 6000 rpm for five minutes at 4° C. Resuspend the pellet in 1/10th volume cold MOPS pH 6.5 with 20% glycerol. Aliquot 200 μl of solution per tube, keeping the solution cold at all times. If the tubes are not to be used immediately, quick freeze the tubes in a dry ice-isopropanol bath. Store the tubes at −70° C.

To transform the competent cells, thaw the cells, if frozen, and add DNA, keeping the volume to 20 μl or less. Leave the suspension on ice for 30 minutes. Heat at 42° C. for two minutes then place the suspension on ice for one minute.

Let the transformed cells equilibrate for four hours at 37° C. to allow expression. Plate 200 μl of the solution per plate on MacConkey agar plates containing 100 μg/ml ampicillin and 1% galactose. Incubate overnight at 30° C.

Pick white colonies and grow these colonies overnight in TY broth with 100 μg/ml ampicillin. Prepare mini-prep DNA by taking 5 ml of cells and pelleting them in a table-top centrifuge. Remove the supernatant and resuspend the pellet in 500 μl 25 mM Tris (pH 8.0), 25 mM EDTA. Add 250 μl of 0.3N NaOH, 2% SDS. Vortex to mix. Place the suspension at 70° C. for 10 minutes then cool to room temperature. Add 80 μl of Phenol:CHCl$_3$(1:1) and vortex well. Centrifuge for 5 minutes. Remove the upper layer and put it in a new Eppendorf tube. Add 70 μl of 3M sodium acetate to the tube then fill the Eppendorf tube with room temperature isopropanol. Incubate 5 minutes at room temperature and then centrifuge at room temperature for an additional 5 minutes. Remove the supernatant. Centrifuge briefly and remove the residual liquid. Dissolve the pellet in 500 μl TE and add 25 μl of 100 mM spermine HCl. Incubate 5 minutes (room temperature) and then centrifuge for 5 minutes at room temperature. Remove the supernatant and resuspend the pellet in 300 μl of 0.3M sodium acetate, 0.01M MgCl$_2$. Add 700 μl of cold ethanol to the suspension. Incubate again at room temperature for 5 minutes and then centrifuge as before. Remove the supernatant, wash with ethanol and dry.

Confirm the presence of inserts by EcoRI digestion of the DNA followed by electrophoresis on a 1% agarose gel. It was found that one of these plasmids contained an insert of about 700 bp. This plasmid was designated pKC377 (BE1392).

Figure 3:
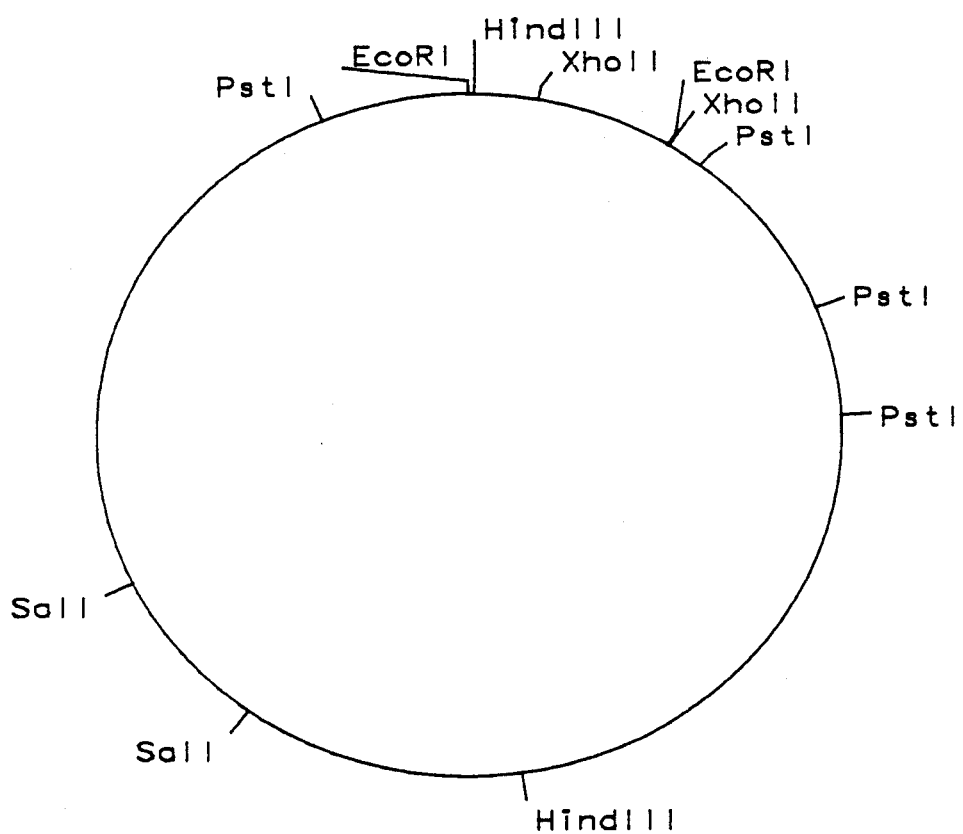
FIG. 3 is a restriction map of plasmid pKC424.

It has been determined that this 700 bp fragment comes from a 3.32 kb EcoRI fragment of pKC331 as shown on the map in FIG. 3. This finding can be confirmed by cutting approximately 20 μg of pKC331 DNA with 25 U EcoRI for two hours at 37° C. in a 100 μl volume. Electrophorese the DNA fragments on a preparative agarose gel to separate the fragments. Transfer the DNA to nitrocellulose by blotting. To transfer, soak gel in 2X volume of 1.5M NaCl, 0.5M NaOH for fifteen minutes. Repeat the soaking step, then soak in 2X volume of 3M NaCl, 1.5M Tris (pH 7.5) for fifteen minutes and repeat the second soak.

Lay two pieces of Whatman 3 MM paper, saturated in 20X SSPE, on a flat support such that the ends of the paper dangle in a tray containing 20X SSPE. Lay the gel on this paper. Place thin strips of Parafilm over the edges of the gel and lay 3 BRL blotting pads saturated with 20X SSPE over the top. Make a 3-inch stack of paper towels on top of the BRL blotting pads. Place a weight on top of the paper towels and allow the stack to set overnight.

Prepare radioactive probes of various clones, in this case using pDR720 with pKC331 inserts. Cut the nitrocellulose filters into strips by cutting perpendicular to the DNA bands. Probe each strip with a different probe.

To probe the strips, take the nitrocellulose filter strip and lay the strip on a few pieces of tissue. Dry in a vacuum oven at 75° for two hours. Put in a plastic bag, add 20 ml of the pre-hybridization mix, seal the bag and incubate at 42° C. for four hours or overnight.

Prepare probe by nick translating. To nick translate, use 1 μg plasmid DNA and add 5 ml of 10X NT Buffer (0.5M Tris, pH 7.8; 0.05 MgCl$_2$; 0.1M mercaptoethanol), 5 μl dXTP mix (300 mM each of dATP, dGTP, TTP) and 20 μCi α-32p-dCTP to form the reaction mixture.

Add H$_2$O to bring the final volume to 50 μl. Dilute 1 mg/ml DNAse 1:10,000 into NT buffer for a 0.1 μg/ml final concentration. Immediately add 1 μl of the DNAse solution to the reaction mixture. Hold the reaction mixture for two minutes at 16° C. Add 1 μl of *E. coli* DNA polymerase I (10 units). Allow the mixture to react for two hours at 16° C. Add 50 μl of 0.1M EDTA and heat at 70° C. for five minutes. Add 10 μl of 0.05% Xylene cyanol and 0.05% bromophenol blue (blue juice) and pass through a prewashed Sephadex G-100 column with a 3 ml bed volume. Collect the first peak as measured with a Geiger counter and ethanol precipitate the DNA present in the eluate. Dissolve the DNA in an appropriate volume of TE. Determine the degree of labeling by Cerenkov counting.

All probes will hybridize to the band containing pBR322 sequences. Choose those clones which also hybridize to the 3.32 kb fragment. To hybridize the probes, dissolve the probes in 250 μl 0.1X TE. Denature by adding 25 μl of 1N NaOH. Incubate for two minutes at room temp. Add 25 μl of 1M Tris (pH 8.0) and 25 μl of 1N HCl. Add enough of this solution to the pre-hybridization mix to result in $10^6$–$10^7$ cpm. A convenient final volume of hybridization mix is 5 ml.

Remove pre-hybridization mix from bag. Add the hybridization mix, squeeze out all the air bubbles and reseal the bag. Incubate at 42° C. with shaking overnight.

Remove filter from bag. Wash with 200 ml 5X SSPE with 0.1% SDS for five minutes at room temp. Wash two times with 200 ml 2X SSPE with 0.1% SDS for fifteen minutes at room temp. Wash one or more times with 200 ml 0.1X SSPE with 0.1% SDS at room temp for fifteen minutes. Continue washing until the background radiation, as determined by scanning with a Geiger counter, is acceptably low. Locate bands hybridized to the filter by autoradiography.

EXAMPLE 3

Construction of Plasmid pKC388

1) Culture of E. coli K12 BE1041/pKC309 and Isolation of Plasmid pKC309

A. Culture

About 5 ml cultures of *E. coli* K12 BE1041/pKC309 (NRRL B-15827) were grown under selective conditions in TY media (1% tryptone, 0.5% yeast extract, 0.5% sodium chloride, pH 7.4) according to conventional microbiological procedures. The cells were spun in a table top centrifuge and the pellet resuspended in 1 ml of 0.3M sucrose, 25 mM EDTA (ethylene diaminetetracetate) and 25 mM Tris-HCl pH 8 (Solution I). After transfer to an Eppendorf tube the cells were centrifuged for about one minute and the pellet was resuspended in 0.5 ml of Solution I. About 50 µl of freshly made lysozyme (20 mg/ml in water) was added and the solution was incubated for 10 minutes at 37° C.

After the addition of 250 µl of freshly made lysis mix (2% sodium dodecyl sulfate and 0.3N NaOH), the cells were immediately and completely vortexed. The cells were then incubated for ten minutes at 70° C., cooled and added to 100 µl of phenol-Sevag (phenol-chloroform-isoamyl alcohol, 25:24:1). After the DNA was centrifuged for two minutes in an Eppendorf centrifuge the supernatant was decanted and transferred to another tube with 70 µl of unbuffered 3M sodium acetate and isopropanol to precipitate the DNA. This solution was incubated for five minutes at room temperature and then centrifuged for two minutes. The supernatant was gently and completely decanted to remove all the excess liquid.

The DNA precipitate was redissolved in 500 µl of TE (10 mM Tris-HCl, pH 8 and 1 mM EDTA) and 25 µl of 100 mM spermine HCl were added. This mixture was vortexed and then incubated for five minutes at room temperature before a five minute spin in an Eppendorf centrifuge. The supernatant was again completely decanted and discarded and the DNA reprecipitated with 1 ml of 75% ethanol, 0.3M sodium acetate, and 10 mM magnesium acetate. This solution was incubated for five minutes at room temperature and the DNA collected as above. The pellet was dissolved in 10 µl of TE for subsequent use as a cloning vehicle.

2) Construction of Plasmid pKC345

A. BclI Digestion of Plasmid pKC309

About 10 µl of plasmid pKC309 DNA were digested in 1X BclI buffer (75 mM KCl, 10 mM Tris pH 7.4, 10 mM MgCl$_2$, and 10 mM DTT) in a total volume of 50 µl with 20 units (New England Biolabs) of BclI restriction endonuclease. The mixture was incubated at 50° C. for about 1½ hours. Next, 0.1 volume of 3M sodium acetate (NaOAc) was added which was followed by 3 volumes of 95% ethanol to precipitate the DNA. This ethanol precipitation was rapidly performed in a dry ice-isopropanol bath. The above procedure for an ethanol precipitation was performed throughout the following experiments unless otherwise indicated. The DNA precipitate was collected by centrifugation in an Eppendorf microfuge for 5 minutes. The DNA pellet was vacuum dried and then suspended in about 10 µl of water for subsequent ligation.

B. Isolation of Plasmid pEL103

1. Culture of *Streptomyces granuloruber* No. A39912.13/pEL103

A vegetative inoculum of *Streptomyces granuloruber* No. A39912.13/pEL103 (NRRL 12549) is conventionally prepared by growing the strain under submerged aerobic conditions in 50 ml of sterilized trypticase soy broth* at 35 g/L in deionized water.

*Trypticase soy broth is obtained from BBL Division, Becton-Dickinson & Company, Cockeysville, Md. 21030

The trypticase soy broth inoculum is incubated for 48 hours at a temperature of 30° C. After incubation, about 10 ml of the inoculum is transferred to 500 ml of the sterilized broth and incubated for about 20 hours at 30° C. The pH is not adjusted. After incubation, the *Streptomyces granuloruber* No. A39912.13/pEL103 cells are ready for harvest and subsequent isolation of plasmid DNA.

2. Plasmid Isolation

About 12 g (wet wgt) of *Streptomyces granuloruber* No. A39912.13/pEL103 cells are centrifuged (10 minutes, 4° C., 10,000 rpm), washed in 10% glycerol, and then harvested by recentrifugation under the aforementioned conditions. About 50 ml of TES buffer (0.01M Tris(hydroxymethyl)aminoethane [Tris], 0.001M EDTA, 34% sucrose, pH 8) are added to the cells followed by about 0.25 g of lysozyme in 10 ml of 0.25M EDTA. After the mixture is incubated at 37° C. for about 15 minutes, about 0.5 ml of 10% Triton X-100 in TE buffer (0.01M Tris, 0.001M EDTA, pH 8) is added. The resultant mixture is then incubated at 65° C. for about 15 minutes. After the lysate is centrifuged (45 minutes, 4° C., 18,000 rpm), the supernatant is extracted four times with isoamyl alcohol and once with a chloroform-isoamyl alcohol solution (24:1). Next, 0.1 volume of 3M sodium acetate is added to the aqueous phase followed by 3 volumes of cold (−20° C.) 95% ethanol. The ethanol precipitation is rapidly performed in a dry ice-ethanol bath and the DNA precipitate collected by centrifugation (15 minutes, 4° C., 10,000 rpm). The precipitate is vacuum dried and then resuspended in 1.1 ml of STE buffer (0.01M Tris, 0.001M EDTA, 0.01M sodium chloride). Centrifugation (40 hours, 15° C., 35,000 rpm) using cesium chloride gradients with ethidium bromide, is carried out to purify the plasmid DNA. Following centrifugation, the desired plasmid pEL103 DNA band is removed and the ethidium bromide extracted by conventional procedures. After precipitation of the DNA in 3 volumes of ethanol, the isolated plasmid pEL103 DNA is dissolved in 1 ml of 10 fold diluted TE buffer and is then stored at −20° C.

3. BamHI Digestion of Plasmid pEL103 and Isolation of the ~2.9 kb Origin of Replication-Containing Fragment About 2 µg of plasmid pEL103 DNA are digested in 1X BamHI buffer (150 mM NaCl, 10 mM Tris pH 8, 10 mM MgCl$_2$) in a total volume of 50 µl with 16 units (New England Biolab) of BamHI restriction endonuclease. The mixture is incubated at 37° C. for 30 minutes. The DNA is ethanol precipitated according to the method of Example 3(2A). Next, the DNA is electrophoresed on a 1% agarose gel until the desired ~2.9 kb BamHI fragment is separated from other fragments. The isolated ~2.9 kb fragment is removed from the gel, placed in a dialysis bag containing 0.5 ml Tris-acetate buffer supplemented with 0.5 μg/ml ethidium bromide and 100 μg/ml BSA and electroeluted at 50-100 V until the DNA is eluted off the gel. Next, the buffer is removed and the DNA extracted with Sevag. The desired ~2.9 kb BamHI restriction fragment is ethanol precipitated and dissolved in TE buffer for subsequent ligation.

C. Construction of Plasmid pKC326 and E. coli K12 BE1041/pKC326

About 2 μg of each of BclI-digested plasmid pKC309 DNA and the ~2.9 kb BamHI Streptomyces origin of replication-containing fragment were ligated in 20 μl of 1X ligase buffer (50 mM Tris pH 7.8, 10 mM MgCl$_2$, 20 mM DTT, and 1 mM ATP) with 400 units of T4 DNA ligase overnight at 16° C. The DNA was ethanol precipitated, dried and redissolved in 5 μl TE for subsequent transformation.

Figure 4:
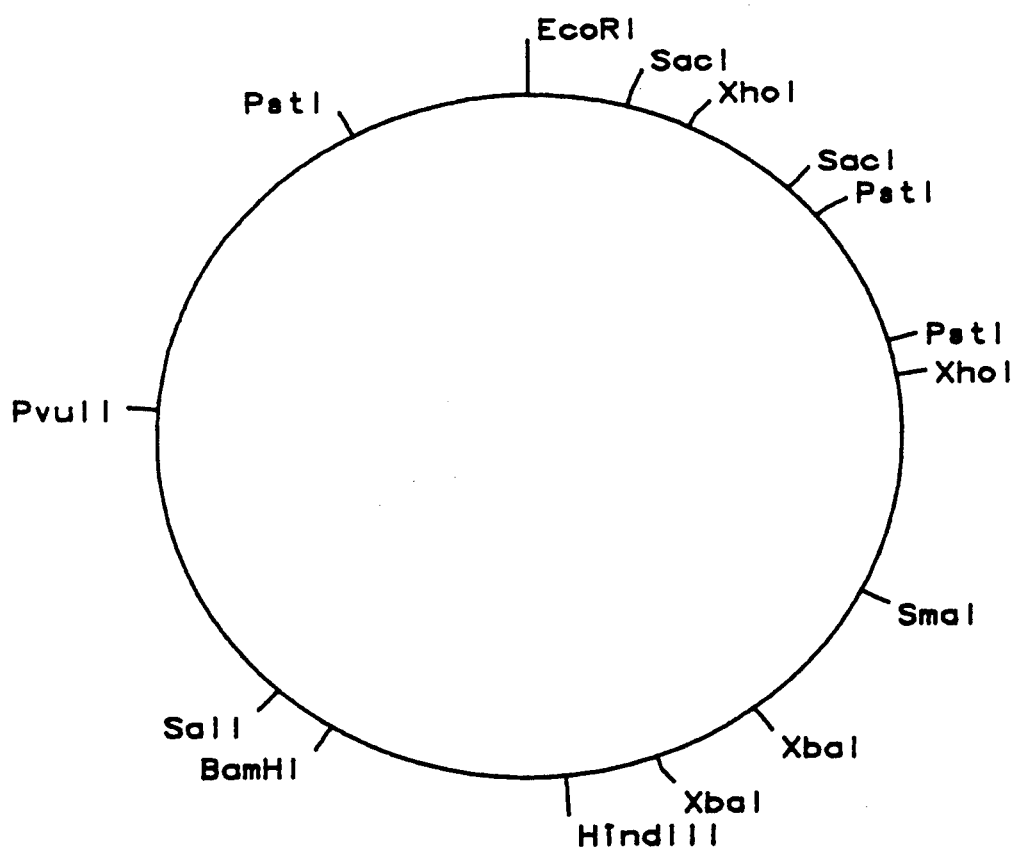
FIG. 4 is a restriction map of plasmid pKC326.

The resultant plasmid DNA was used to transform E. coli K12 BE1041 (NRRL B-15021) according to the procedure of Maniatis et al., 1982. The identity of the desired transformants was conventionally confirmed by screening for the acquisition of a PstI site. The resultant E. coli K12 BE1041/pKC326 transformants were conventionally cultured for subsequent production and isolation of plasmid pKC326. A restriction site and functional map of plasmid pKC326 is presented in FIG. 4 of the accompanying drawings.

D. Final Construction of Plasmid pKC345

1. BamHI Digestion of Plasmid pKC326

About 2 μg of plasmid pKC326 DNA were digested with BamHI restriction enzyme in substantial accordance with the teaching of Example 3 (2B(3)), except that the digestion was carried out for 1 hour. The DNA was ethanol precipitated, dried and redissolved in 5 μl TE buffer for subsequent ligation to a thiostrepton resistance gene isolated from plasmid pIJ702.

2. BclI Digestion of Plasmid pIJ702 and Isolation of the ~1 kb Thiostrepton Resistance-Conferring Gene About 5 μg of plasmid pIJ702 DNA (ATCC 39155) are digested with BclI restriction enzyme in substantial accordance with the teaching of Example 3(2A). The DNA is ethanol precipitated, dried and then dissolved in 5 μl TE. The DNA is electrophoresed on a 1% agarose gel until the desired ~1 kb BclI fragment is separated from other fragments. Whatman DEAE cellulose paper is placed in a slit prepared ahead of the desired DNA band and the DNA is electrophoresed onto the DEAE paper. The paper is washed with 1 ml of TE and the DNA is eluted with 400 μl of TE adjusted to 1M by the addition of an appropriate volume of NaCl. The eluted DNA is ethanol precipitated and finally dissolved in 5 μl of TE.

3. Ligation and Construction of E. coli K12 BE1041/pKC345

About 2 μg of BamHI-digested plasmid pKC326 DNA and ~5 μg of the ~1 kb BclI restriction fragment of plasmid pIJ702 DNA were ligated in substantial accordance with the teaching of Example 3(2C). After ethanol precipitation, the DNA was further digested with BamHI restriction enzyme to reduce the number of parental plasmids.

Figure 5:
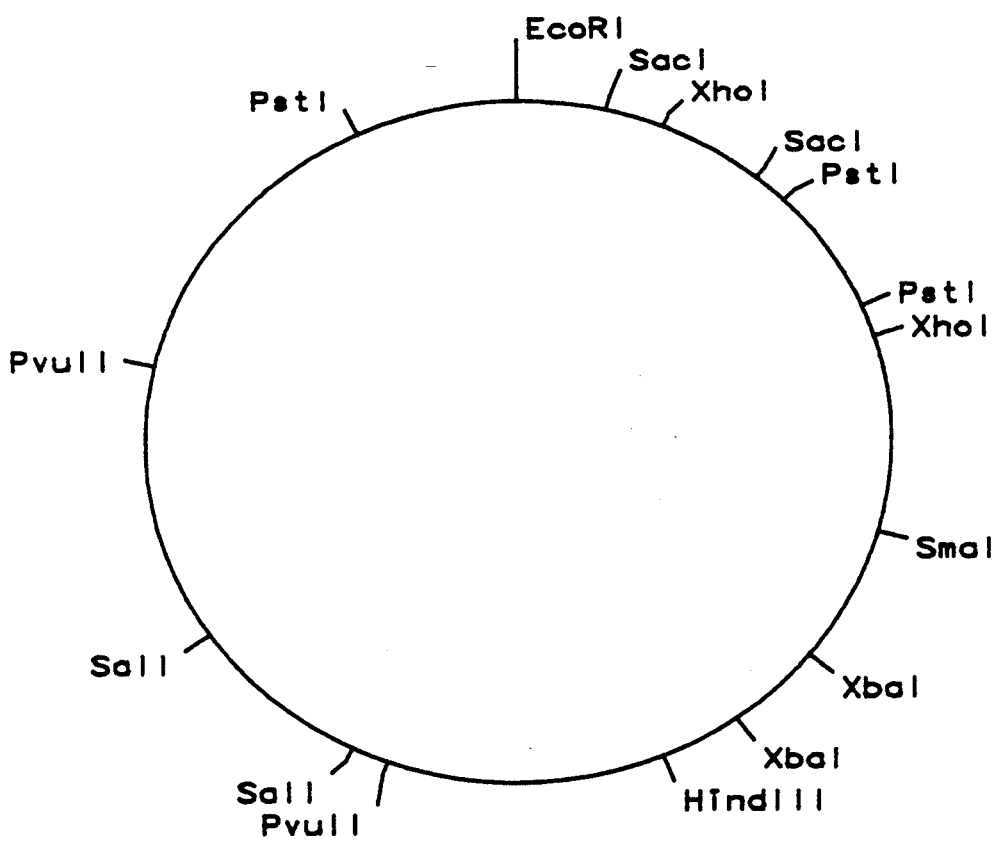
FIG. 5 is a restriction map of plasmid pKC345.

The resultant DNA was used to transform E. coli K12 BE1041 according to the procedure of Maniatis et al., 1982. The identity of the desired transformants was conventionally confirmed by screening for ampicillin resistance, tetracycline sensitivity and the acquisition of a SalI site. Transformed cells were conventionally cultured for subsequent production and isolation of plasmid pKC345. A restriction site and functional map of plasmid pKC345 is presented in FIG. 5 of the accompanying drawings.

3) Construction of pKC354 and E. coli K12 BE1041/pKC354

A. AvaI Digestion of pKC322 and Isolation of the ~2.1 kb AvaI Restriction Fragment About 150 μg of plasmid pKC322 DNA (NRRL B-15829) were digested in 1X AvaI buffer (60 mM NaCl, 10 mM Tris pH 8, 10 mM DTT and 10 mM MgCl$_2$) in a total volume of 1 ml with 15 units (New England Biolabs) of AvaI restriction enzyme for 7 hours at 37° C. Another 20 units of AvaI restriction enzyme were added and the reaction was continued overnight. The resulting DNA, in the digestion buffer, was electrophoresed overnight at 50 V on a 1% agarose gel in substantial accordance with the teaching of Maniatis et al., 1982.

The ~2.1 kb band was isolated from the gel and the DNA eluted from the gel in substantial accordance with the teaching of Example 3(2B(3)). The DNA was extracted twice with phenol and twice with Sevag (chloroform-isoamyl alcohol, 24:1). The ~2.1 kb AvaI fragment was purified using an Elutip-d column (Schleicher and Schuell, Inc., Keene, N.H. 03431) and then precipitated with ethanol and redissolved in 20 μl TE. An equivalent method to purify DNA fragments can also be used whereby the DNA is electrophoresed on a 1% agarose gel until the desired fragment is separated from other fragments. Whatman DEAE cellulose paper is then placed in a slit prepared ahead of the desired DNA band and the DNA is electrophoresed onto the DEAE paper. The paper can then be washed with 1 ml TE and the DNA eluted with 400 μl TE which is adjusted to 1M by the addition of an appropriate volume of NaCl. The eluted DNA is ethanol precipitated and dissolved in 5 μl TE for subsequent ligation.

B. SacI Digestion of Plasmid pKC345

About 10 μg of plasmid pKC345 DNA were digested in 1X SacI buffer (10 mM MgCl$_2$, 10 mM Tris pH 7.4, and 10 mM DTT) in a total volume of 10 μl with 5 units (New England Biolabs) of SacI restriction endonuclease for 1 hour at 37° C. The reaction was terminated by increasing the temperature to 70° C. for 5 minutes.

C. Ligation to Construct Plasmid pKC354

About 5 μl each of the purified ~2.1 kb AvaI restriction fragment and the SacI-digested pKC345 were added to 2 μl of 10X T4 polymerase buffer (67 mM potassium acetate, 33 mM Tris-acetate pH 7.8, and 10 mM Magnesium acetate). Next, 1 μl of 20X deoxynucleotides (dATP, dGTP, dCTP, TTP; final concentration was 10 μM) was added and the volume adjusted to 20 μl with water. After 1 μl of T4 DNA polymerase was added the mixture was incubated at 37° C. for 5 minutes. This last step was repeated and then 2 μl of 50 mM EDTA was added and the reaction was terminated by increasing the temperature to 70° C. for 5 minutes. The DNA was extracted once with Sevag and after the volume was increased to 50 μl with water, the DNA was ethanol precipitated to remove the T4 polymerase salts. The DNA precipitate was suspended in 20 μl of T4 DNA ligase buffer supplemented with 400 units of T4 DNA ligase (NEB) and the ligation was run at 16° C. for 48 hours.

D. Transformation and Construction of *E. coli* K12 BE1041/pKC354

Figure 6:
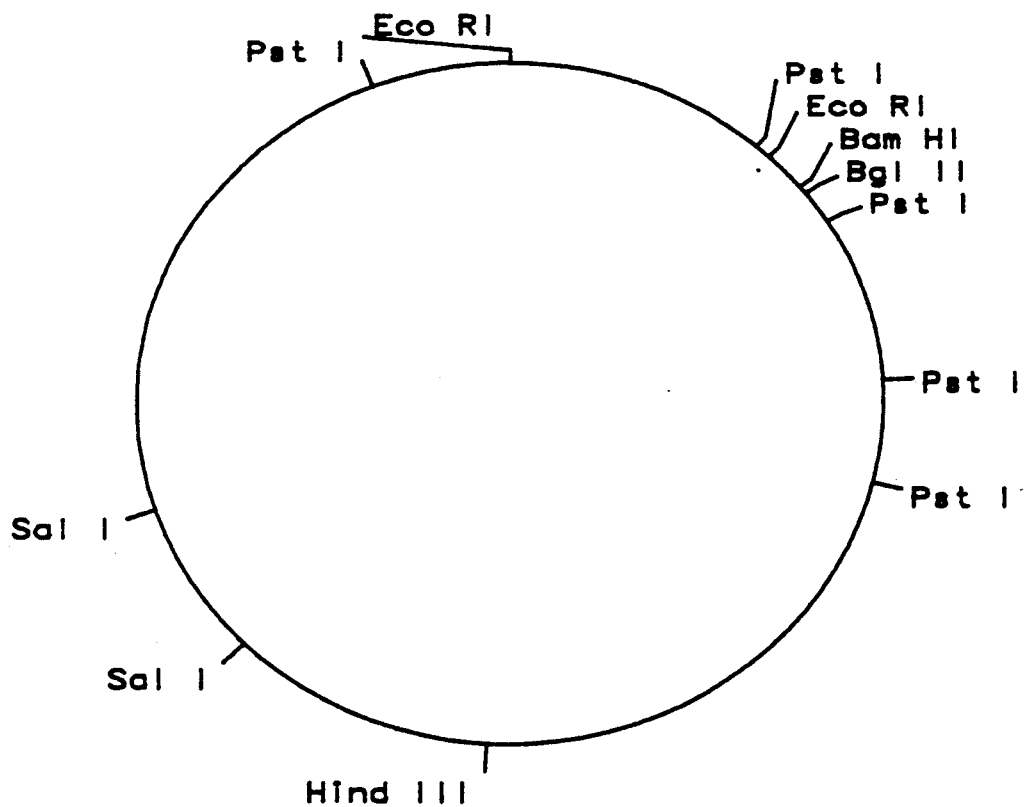
FIG. 6 is a restriction map of plasmid pKC354.

About 1 μl of the ligated DNA was used to transform *E. coli* K12 BE1041 according to the procedure of Maniatis et al., 1982. The transformants were conventionally screened using colony hybridization and a probe prepared by nick translating 2 μl of the purified ~2.1 kb AvaI restriction fragment. The identity of the desired transformants was conventionally confirmed by screening for ampicillin resistance and the acquisition of an EcoRI site, a BamHI site and a BglII site. Transformed cells were conventionally cultured for subsequent production and isolation of plasmid pKC354. A restriction site and functional map of plasmid pKC354 is presented in FIG. 6 of the accompanying drawings.

4) Construction of Plasmid pKC356 and *E. coli* K12 BE1041/pKC356

A. EcoRI Digestion of Plasmid pKC354

Plasmid pKC356 was constructed by deleting an ~1.5 kb EcoRI fragment from plasmid pKC354. About 10 μg of pKC354 DNA were digested in 1X EcoRI buffer (100 mM Tris pH 7.5, 50 mM NaCl, and 10 mM $MgCl_2$) in a total volume of 20 μl with 24 units (New England Biolabs) of EcoRI restriction enzyme for 1 hour at 37° C. The resulting fragments were isolated by agarose gel electrophoresis and the ~11 kb EcoRI restriction fragment was extracted with phenol and Sevag, purified on an Elutip-d column and ethanol precipitated. The DNA precipitate was redissolved in 10 μl TE for subsequent ligation.

B. Ligation and Transformation

The resultant DNA was ligated in substantial accordance with the teaching of Example 3(2C) and incubated at 16° C. overnight to promote self-circularization. After incubation, the DNA was ethanol precipitated and dissolved in 10 μl TE.

Figure 7:
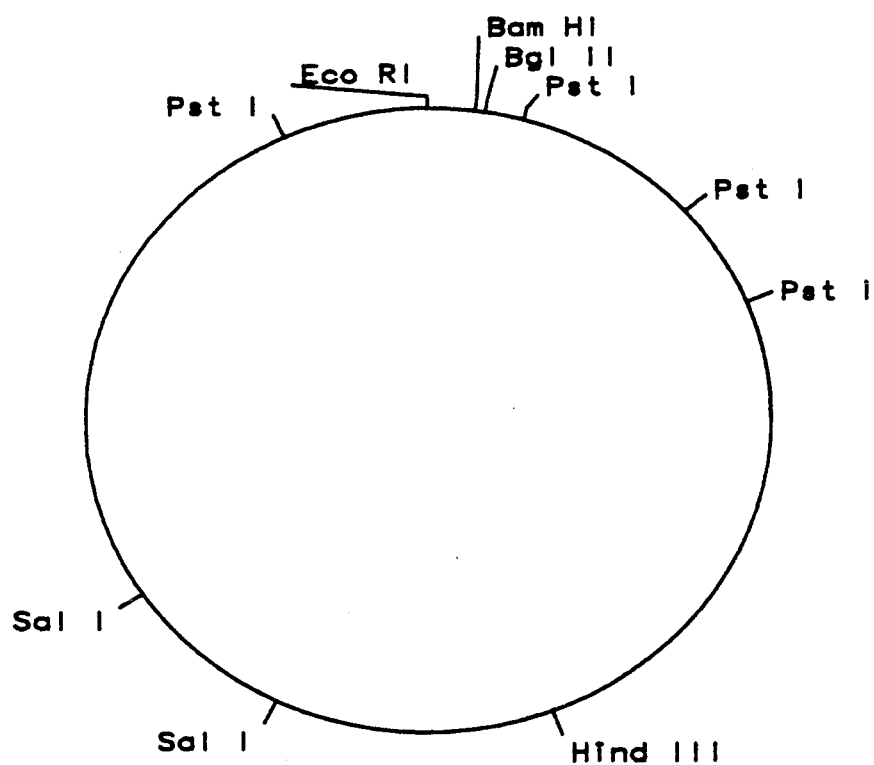
FIG. 7 is a restriction map of plasmid pKC356.

About 2 μl of the resultant DNA were used to transform *E. coli* K12 BE1041 in substantial accordance with the teaching of Maniatis et al., 1982. The identity of the desired transformants was conventionally confirmed by screening for ampicillin resistance and for the deletion of an EcoRI restriction site. Transformed cells were conventionally cultured for subsequent production and isolation of plasmid pKC356. A restriction site and functional map of plasmid pKC356 is presented in FIG. 7 of the accompanying drawings.

5) Construction of Plasmid pKC388

Five μl of a stock solution of plasmid pKC7 (ATCC 37084) are digested for 1 hr at 37° C. in 50 μl of buffer with 50 units of PstI. A 10 μl aliquot is examined by gel electrophoresis to monitor the extent of digestion. The DNA solution is extracted with phenol:$CHCl_3$ (1:1) and precipitated with ethanol. The precipitated DNA is then digested with 25 units of EcoRI for 30 minutes at 37° C. in 50 μl of buffer.

One μg of plasmid pKC356 is also digested with EcoRI as set forth above. The two digests are then pooled and precipitated with ethanol. The pooled DNA is digested with 16 units of BglII in 100 μl of buffer for 40 min at 37° C. and then precipitated with ethanol. The pooled DNA comprising digests of pKC7 and pKC356 is ligated overnight with 400 units of T4 DNA ligase in 30 μl of buffer at 16° C. The *E. coli* strain BE1041 (NRRL B-15021) is transformed with 10 μl of the ligated DNA. The transformed hosts were incubated about 6 hours at 37° C. to allow expression of the plasmid genes. About 0.1 ml of the transformed *E. coli* K12 BE1041 is then plated on TYAp100Nm25 plates. Colonies which grow on these plates are isolated and grown overnight at 30° C. in TYAp100Nm25 broth. A Kieser mini-prep of DNA is done and the presence of the neomycin promoter is confirmed by digesting the DNA with HindIII in 15 μl of buffer for 2 hours at 37° C.

EXAMPLE 4

Construction of Plasmid pKC409

Cut 27 μg of pKC377 (from Example 2 or NRRL B-15885) with 25 U EcoRI (obtained from New England Biolabs, lot 15) for 1½ hours at 37° C. in a 50 μl volume. Adjust the volume to 400 μl and electrophorese on a 1% agarose gel. Cut a slit in front of the 700 bp band and place a piece of DEAE paper (Whatman) in front of the band. Electrophorese the DNA into the paper. Elute the DNA with 300 μl TE with 1M NaCl for 5 minutes at room temperature. Remove the TE-NaCl and add an additional 200 μl of the TE-NaCl solution to the paper as a wash and remove. Pool the two fractions and add 1 ml ethanol. Chill in a dry ice-ethanol bath for five minutes. Centrifuge in an Eppendorf microfuge for five minutes. Remove the supernatant and wash the pellet with ethanol. Dry the pellet under a vacuum then dissolve in 10 μl TE.

Cut approximately 10 μg of pUC8, obtainable from BRL with 25 U EcoRI for one hour at 37° C. in 20 μl. Do 1 sevag extraction and ethanol precipitate. Dissolve in 10 ml TE.

Ligate 5 μl of the purified EcoRI fragment to 1.5 μl of the cut pUC8 with 400 U T4 DNA ligase overnight at 16° C. in 20 ml.

Transform BE1510 (JM101, available from New England Biolabs, Inc., Beverly, Mass.) with 10 μl of this DNA solution by the transformation process set forth above. Let the transformants express for three hours at 37° C. Plate 0.1 ml of the transformed cells on TY with 100 μg/ml ampicillin, 40 μg/ml XG, and 1 m M IPTG. Pick white colonies and grow these cells overnight in 10 ml TY+100 μg/ml ampicillin. Prepare mini-prep DNA from 5 ml by the method set forth above and determine correct orientation of the insert by digestion with BamHI by dissolving the DNA in 100 μl TE and cutting 5 μl with 16 U BamHI for one hour at 37° C. in a 15 μl volume.

EXAMPLE 5

Construction of Plasmids pKC424 and pKC425

Cut approximately 5.2 μg pKC388 with 12 U BglII for one hour at 37° C. in 50 μl. Add 5 μl of 10X IBI BAP buffer, 40 μl $H_2O$ and 5 μl IBI bacterial alkaline phosphatase (0.25 U). Incubate at 70° C. for one hour. Do 1 phenol and 1 sevag extraction. Ethanol precipitate the DNA by the method set forth above.

Cut 5 μl of mini-prep pKC409 with 6 U AhaIII for two hours at 37° C. in 50 μl volume. Ethanol precipitate the DNA as above. Cut with 16 U BamHI for one hour at 37° C. in 20 μl volume. Take one-half of the volume and ethanol precipitate the DNA.

Dissolve the pKC388 DNA in 11 μl TE. Add 2 μl of the dissolved pKC388 DNA to the precipitated pKC409 DNA and ligate overnight at 16° C. in 20 μl with 400 U T4 DNA ligase.

Figure 8:
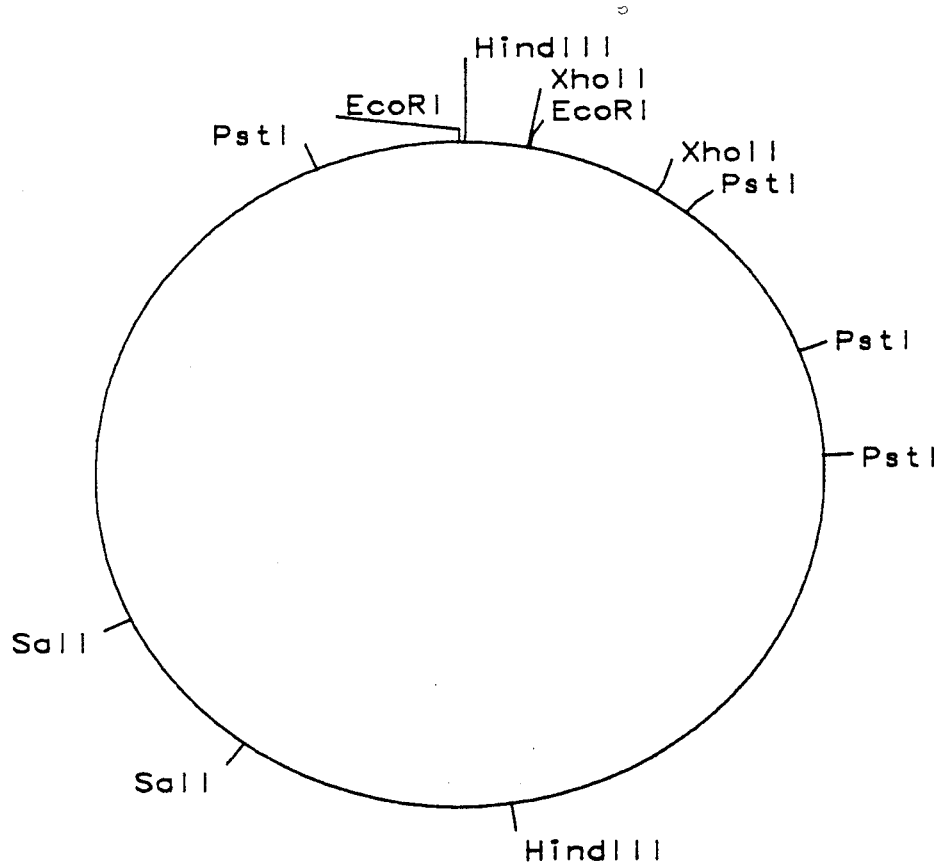
FIG. 8 is a restriction map of plasmid pKC425.

Transform *E. coli* K12 BE1041 (NRRL B-15021) with 10 μl of the ligated DNA using the method set forth above. Allow the transformed cells to express for three hours at 37° C. Plate 0.1 ml on TY plates with 100 μg/ml ampicillin and incubate at 37° C. Pick transformants and grow the transformants overnight in 10 ml TY with 100 mg/ml ampicillin. Prepare mini-prep DNA from 5 ml of the broth by the above method and dissolve in 100 μl TE. Cut 10 μl of each mini-prep with 20 U EcoRI for one hour at 37° C. in 20 μl. A plasmid with the insert in each orientation was chosen and designated pKC424 and pKC425. A restriction site map of plasmid pKC425 is presented in FIG. 8 of the accompanying drawings.

EXAMPLE 6

Construction of *Streptomyces ambofaciens*/pKC424 and *Streptomyces ambofaciens*/pKC425

*Streptomyces ambofaciens* (NRRL 2420) protoplasts were transformed with pKC424 and with pKC425 by thawing a tube of protoplasts containing 200 μl per tube. Add 0.4 ml of P medium and take 200 μl of this solution and add to the plasmid. Add 0.5 ml of 55% polyethylene glycol (PEG) in P medium. Mix the suspension for one minute at room temperature. Add approximately 10 μl 100 ml of the suspension to 3 ml of R2 overlay media and pour onto R2 plates. Tilt the plates to spread the agar then allow the agar to set. Incubate overnight at 30°. Select for transformants by overlaying with thiostrepton at a final concentration of 25 mg/ml. To overlay with a drug, add the drug to 3 ml of the R2 overlay. Pour the overlay onto plates which have protoplasts spread on them. This is done the day after the transformation. Incubate the plates at 30°. Preferably, the following concentrations are used:

Thiostrepton: 25 μg/ml final concentration
Neomycin: 10 μg/ml final concentration Pick transformants and grow in TSB broth with 25 μg/ml thiostrepton. Prepare mini-prep DNA and confirm the structure by cutting with EcoRI.

Additionally, *Streptomyces ambofaciens*/pKC424 and *S. ambofaciens*/pKC425 can be prepared in substantial accordance with the teaching of U.S. Pat. No. 4,468,462 and International Publication Number WO79/01169, the relevant teachings of which are incorporated by reference herein. The procedures disclosed and incorporated in this Example 5 are applicable to Streptomyces species generally.

EXAMPLE 7

Neomycin Phosphotransferase Assays

About 250 ml of overnight cultures of Streptomyces are grown in TSB broth with 25 ug/ml thiostrepton, and *E. coli* cultures are grown in TY broth with 100 μg/ml ampicillin. Centrifuge the suspensions at 10,000 rpm for 10 minutes. Wash the cell pellet with 100 ml of 10 mM Tris pH 8.0. Centrifuge and wash again. Centrifuge for a third time and resuspend the cells in 5 ml 10 mM Tris pH 8.0, 0.5 mM MgCl₂, 0.1 mM EDTA, 1 mM DTT. Sonicate the cells for 5 bursts of 15 seconds each with the sonifier set on high. Keep the sonicated cells on ice and allow the extract to cool for 30 seconds between bursts. Centrifuge at 16,000 rpm in a SS34 rotor for 30 minutes at 4° C. Remove the supernatant. Add DNAse to the suspension to a final concentration of 4 μg/ml. Centrifuge at 45,000 rpm in a 75 Ti rotor for 2 hr at 40° C. Remove the supernatant and estimate protein concentration as follows:

Dilute 100-fold into water. Take absorption readings at 260 and 280 nm.

Concentration = 100 × [(1.5 XA280) − (0.75 XA260)]

Phosphotransferase Assay

Reaction Mix 4 mM Neomycin—Make as a 10X stock
13 mM Tris pH 8.0—Make as a 10X stock
8.4 mM MgCl₂—Make as a 10X stock
80 mM NH₄Cl—Make as a 10X stock
2 mM DTT—10X stock
2 mM ATP—make 10 x stock, this is cold ATP plus γ−³²P-ATP so the final specific activity is 9–10 μCi/μmole
40 μg Protein extract Add everything except protein. The total reaction volume is 50 μl. Add 40 μg protein and vortex to mix. Incubate the mixture at 30° C. for 15 minutes. Take 25 μl and pipet onto Whatman P-81 filters. Place the filters in an 80° C. water bath for 5 minutes then wash the filters under running water for 15 minutes. Dry the filters and count.

| | Expression of Nm Phosphotransferase in *E. coli* and *S. ambofaciens* | | | | |
|---|---|---|---|---|---|
| | *E. coli* | | | *S. ambofaciens* | |
| | CPM | | % | CPM | | % |
| Plasmid | + | − | Term | + | − | Term |
| none | 261 | 46 | | 65 | 48 | |
| pKC388 | 44,000 | 44 | | 40,700 | 84 | |
| pKC424 | 335 | 51 | >99% | 1,975 | 1,262 | 95% |
| pKC425 | 5,550 | 73 | 87% | 177 | 159 | >99% |

+ indicates neomycin included in reaction
− indicates no substrate

The above results indicate that cells harboring plasmids pKC424 or pKC425 were sensitive to neomycin and that the level of the neomycin phosphotransferase activity was reduced by at least 87%. Thus, the present invention is clearly effective for terminating transcription. It will be apparent to those skilled in the art that various modifications and variations can be made in the processes and products of the present invention. Thus, it is intended that the present invention cover the modifications and variations of this invention provided they come within the scope of the appended claims and their equivalents.

We claim:

1. A segment of recombinant DNA comprising a transcription terminator of bacteriophage φC31.

2. The transcription terminator of claim 1 wherein said terminator is capable of reducing transcription of an adjacent DNA sequence in microorganisms of the family Streptomycetaceae.

3. The transcription terminator of claim 1 wherein said terminator is capable of reducing transcription of an adjacent DNA sequence in microorganisms of the genus Streptomyces.

4. The transcription terminator of claim 1 wherein said terminator is capable of reducing transcription of an adjacent DNA sequence in microorganisms selected from the group consisting of Streptomyces, Nocardia and Cephalosporium.

5. The transcription terminator of claim 1 wherein said terminator is capable of reducing transcription of an adjacent DNA sequence in *Streptomyces ambofaciens*.

6. The transcription terminator of claim 1 wherein said terminator is capable of reducing transcription of an adjacent DNA sequence both in gram-negative and gram-positive organisms.

7. The transcription terminator of claim 6 wherein said terminator is capable of reducing transcription of an adjacent DNA sequence in organisms selected from the group consisting of Streptomyces and Escherichia.

8. The transcription terminator of claim 1 wherein the terminator is functionally bi-directional and operative regardless of orientation within said recombinant vector.

9. A restrictionless Streptomyces host cell comprising a transcription terminator of claim 1.

10. A segment of recombinant DNA according to claim 1 wherein said transcription terminator is isolated from the 3.3 kilobase EcoRI restriction fragment of bacteriophage φC31.

11. A segment of recombinant DNA according to claim 10 wherein said transcription terminator contains approximately 700 base pairs.

12. A recombinant DNA cloning vector comprising an origin of replication operable in a microorganism, a promoter, at least one gene associated with and capable of being transcribed when initiated by said promoter, and a transcription terminator of claim 1, wherein said terminator is located in said cloning vector in a position such that it is capable of reducing readthrough transcription of an adjacent DNA sequence when said cloning vector is transformed into said microorganism.

13. The recombinant vector of claim 12 wherein said transcription terminator is located upstream from said promoter.

14. The recombinant cloning vector of claim 13 wherein said transcription terminator is located 10 to 20 base pairs upstream of said promoter.

15. The recombinant cloning vector of claim 12 wherein said vector comprises at least two genes and said transcription terminator is located in a position wherein at least one gene is transcribed and wherein transcription of at least one other gene is reduced.

16. The recombinant cloning vector of claim 12 wherein said portable DNA sequence is located between said promoter and said gene.

17. The recombinant cloning vector of claim 12 wherein said vector comprises at least two transcription terminators, at least one terminator located upstream from said promoter and at least one terminator located downstream from said gene.

18. The recombinant cloning vector of claim 17 wherein one transcription terminator is located 10 to 20 base pairs upstream of said promoter and wherein another transcription terminator is located 10 to 20 base pairs downstream from said gene associated with said promoter.

19. The recombinant cloning vector of claim 12 wherein said vector comprises at least two transcription terminators located in juxtaposition to each other.

20. The recombinant cloning vector of claim 12 wherein said transcription terminator is located 10 to 20 base pairs downstream from said gene associated with said promoter.

21. A restrictionless Streptomyces host cell comprising a vector of claim 12.

22. A recombinant DNA cloning vector comprising a terminator of claim 1.

23. A restrictionless host cell comprising a vector of claim 22.

24. The host cell of claim 23 which is *E. coli*.

25. The host cell of claim 24 which is *E. coli* K12 BE1041/pKC424.

26. The host cell of claim 23 which is *Streptomyces ambofaciens*/pKC424.

27. The host cell of claim 23 which is *Streptomyces ambofaciens*/pKC425.

28. A method for reducing the transcription of a portion of a recombinant DNA cloning vector which comprises inserting, into said vector, at least one transcription terminator of claim 1 capable of reducing transcription in a microorganism of the genus Streptomyces and inserting said vector into a 29. The method of claim 28 wherein said vector is inserted into a microorganism selected from the group consisting of restrictionless Streptomyces, Nocardia and Cephalosporium.

30. The method of claim 28 wherein said terminator is positioned upstream from a promoter which comprises said vector.

31. The method of claim 28 wherein said terminator is positioned downstream from a gene and associated promoter which comprises said vector.

32. The method of claim 28 wherein said vector comprises at least two terminators.

33. The method of claim 32 wherein at least one terminator is positioned upstream and wherein at least one terminator is positioned downstream from a promoter and associated gene which comprises said vector.

34. The method of claim 33 wherein a terminator is located 10–20 base pairs upstream and wherein another terminator is located 10–20 base pairs downstream from said promoter and associated gene which comprises said vector.

35. The method of claim 34 wherein said vector is inserted into a restrictionless host cell.

36. The method of claim 35 wherein said host cell is Streptomyces.

37. The method of claim 36 wherein the host cell is *Streptomyces ambofaciens*.

38. A recombinant DNA cloning vector selected from the group consisting of plasmids pKC424, pKC425, pKC377 and pKC331.

39. The recombinant DNA cloning vector of claim 38 which is plasmid pKC424.

40. The recombinant DNA cloning vector of claim 38 which is plasmid pKC425.

* * * * *